United States Patent
De La Plaza Fernandez

[11] Patent Number: 6,036,690
[45] Date of Patent: Mar. 14, 2000

[54] LINEAR EXPANDER FOR THE PROGRESSIVE CORRECTION OF CRANIOFACIAL DEFORMATIONS

[76] Inventor: Rafael De La Plaza Fernandez, Salou, 28, E-28034, Madrid, Spain

[21] Appl. No.: 08/809,300

[22] Filed: Feb. 21, 1997

Related U.S. Application Data

[63] Continuation of application No. PCT/ES96/00079, Apr. 9, 1996.

[51] Int. Cl.$^7$ .................................................. A61B 17/56
[52] U.S. Cl. ................................................................ 606/53
[58] Field of Search .................................. 606/53, 54, 55

[56] References Cited

U.S. PATENT DOCUMENTS

| | | | |
|---|---|---|---|
| 3,976,060 | 8/1976 | Hildebrandt et al. | 606/53 |
| 4,157,715 | 6/1979 | Westerhoff | 606/53 |

FOREIGN PATENT DOCUMENTS

| | | |
|---|---|---|
| 2267080 | 11/1975 | France . |
| 2713837 | 3/1978 | Germany . |
| 8802618 | 4/1988 | WIPO . |
| 9418897 | 9/1994 | WIPO . |
| 9422400 | 10/1994 | WIPO . |

*Primary Examiner*—Michael Buiz
*Assistant Examiner*—(Jackie) Tan-Uyen T. Ho
*Attorney, Agent, or Firm*—Ladas & Parry

[57] ABSTRACT

Linear expander for progressive correction of craniofacial deformations. It consists in two elements which are movable longitudinally with respect to one another, are driven by an actuating element arranged between them and are intended to cause mutual displacement of the portions of tissue to which they are applied by means of the injection of a fluid. The expander also comprises an inflatable element, made of flexible and elastic material, which actuates a movable element adapted to cause separation of the bony tissue to which it is applied from the remainder of the bony tissue anchored to the fixed element of the expander. Said movable element has its free end shaped as a hook in order to be applied under the edge of the portion of bony tissue opposite that in which the fixed element, which may have a similar hook, is anchored.

26 Claims, 6 Drawing Sheets

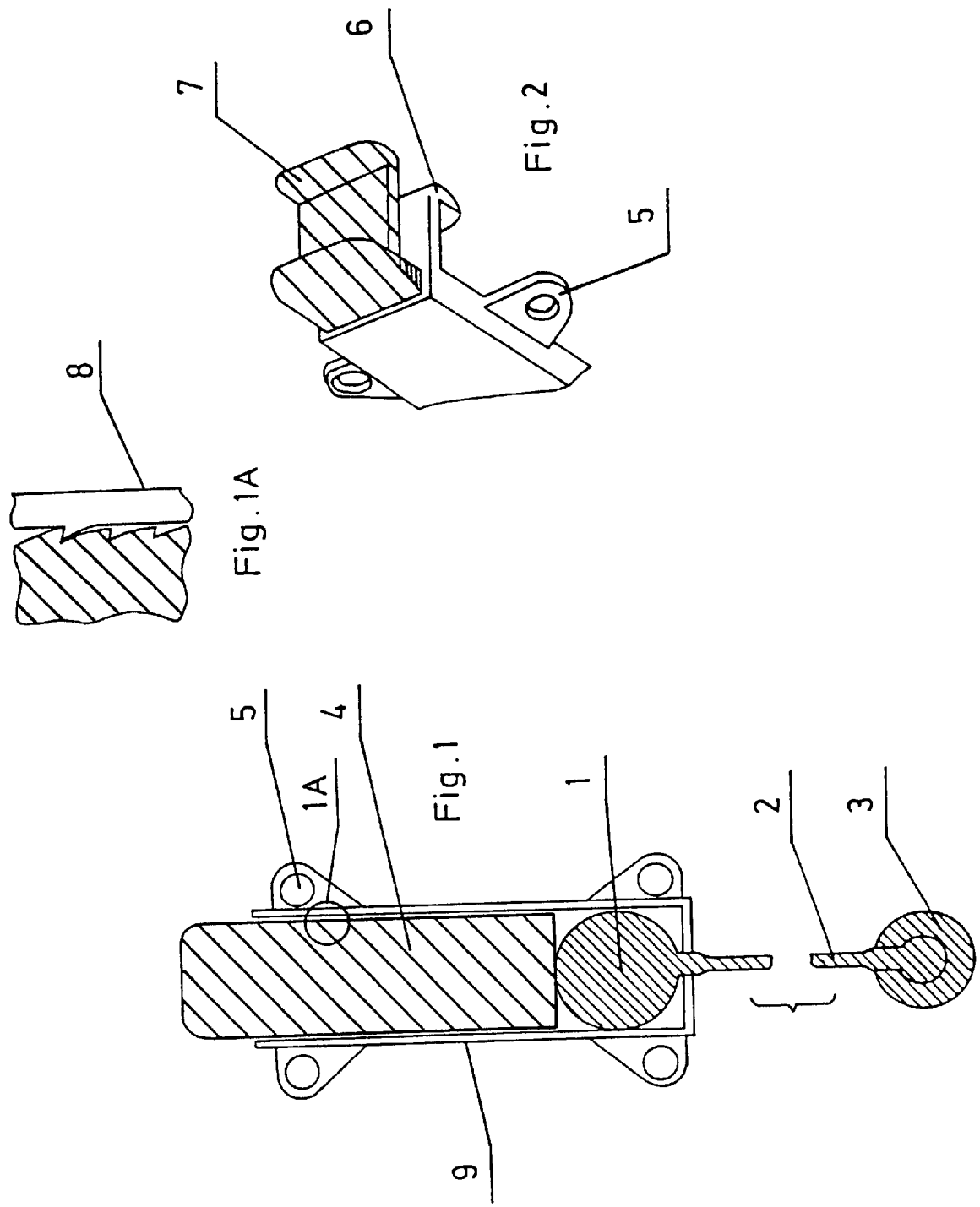

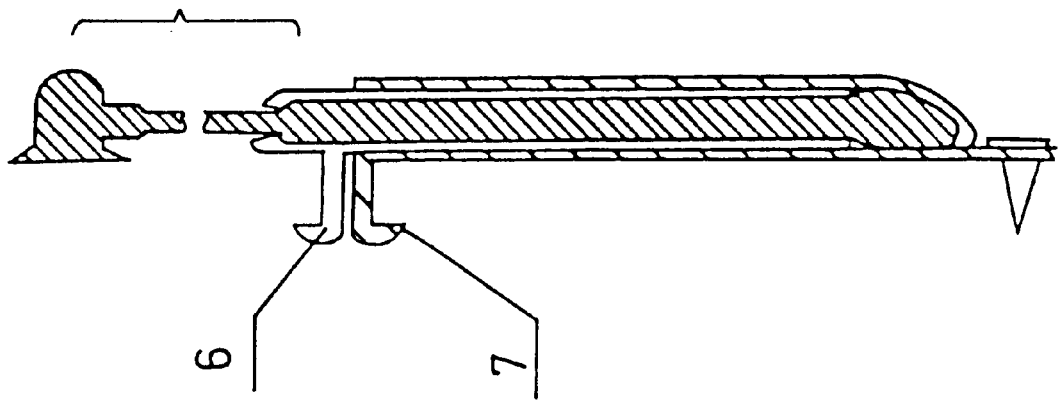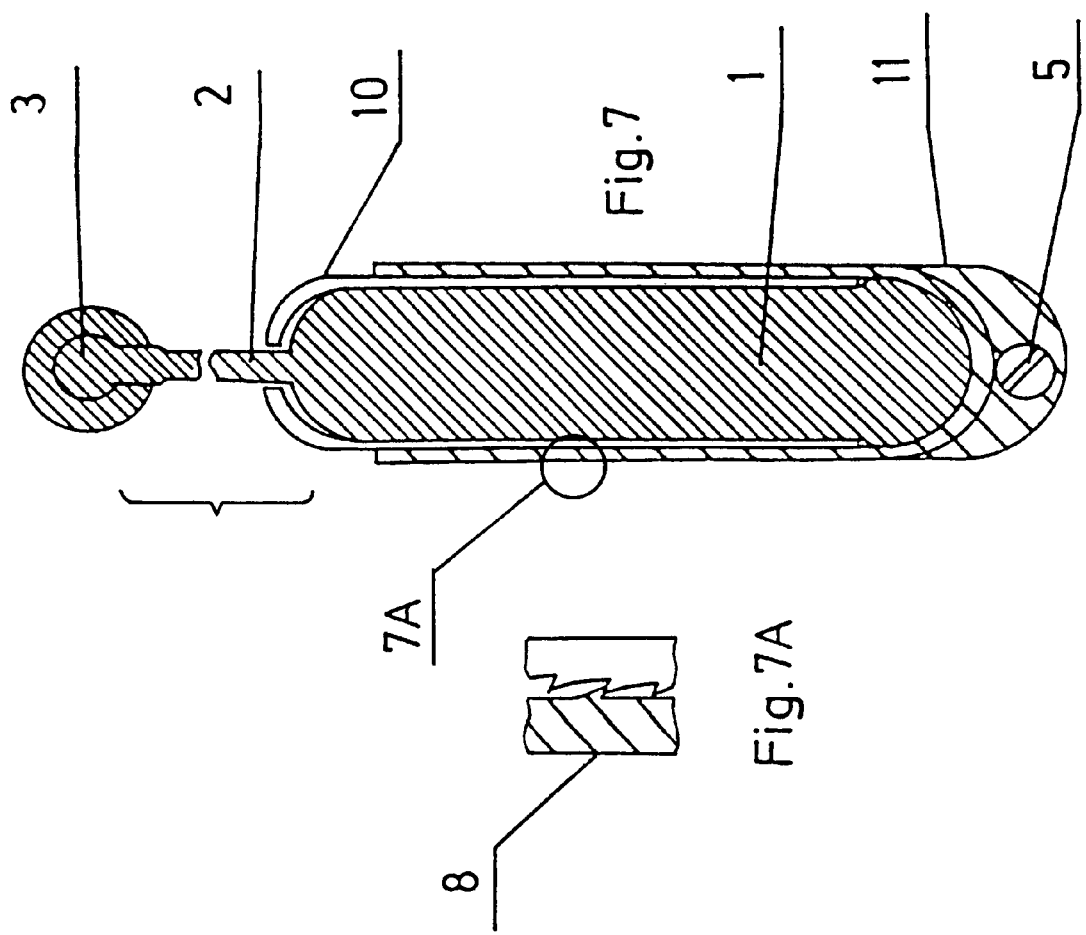

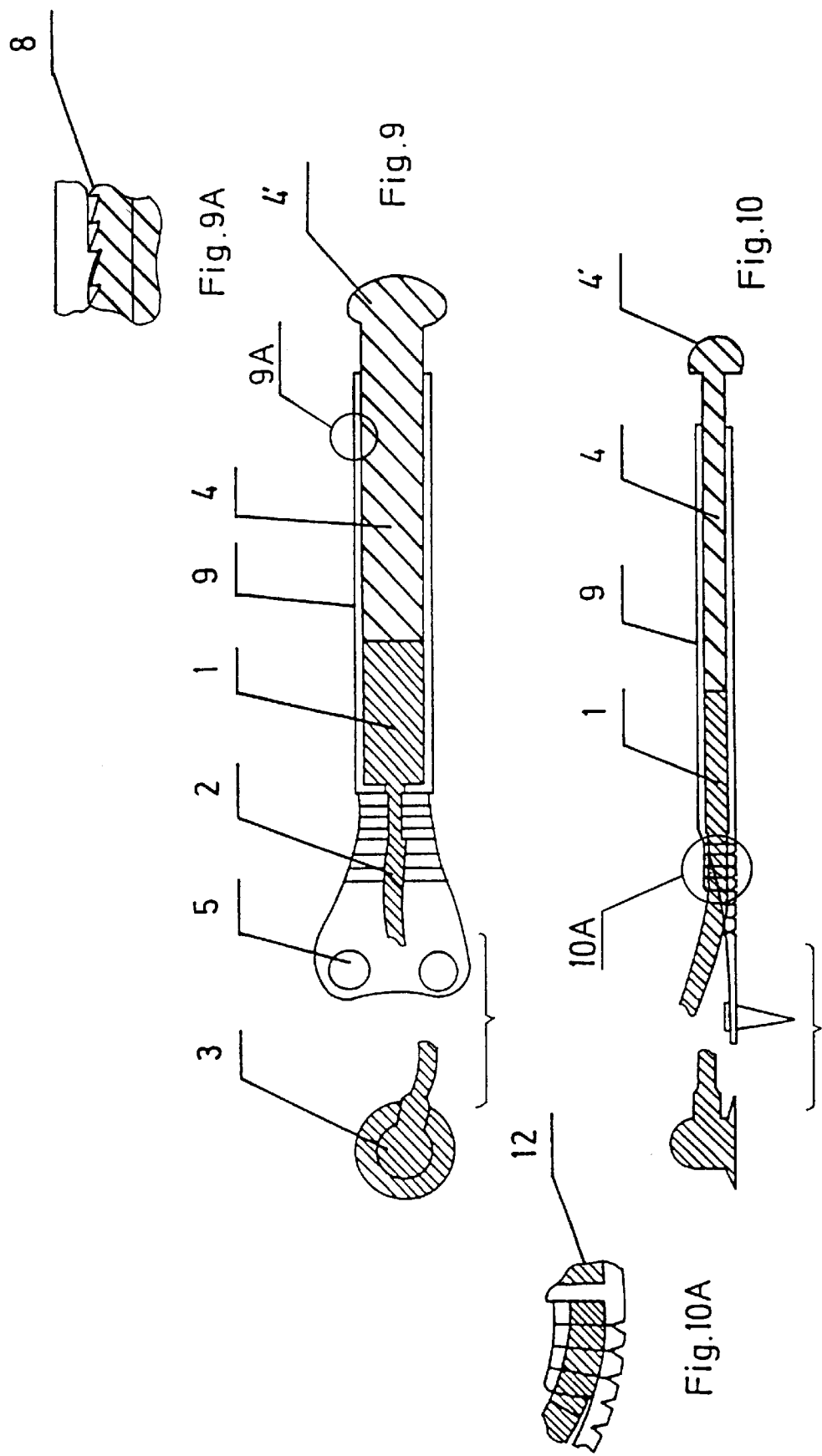

LINEAR EXPANDER FOR THE PROGRESSIVE CORRECTION OF CRANIOFACIAL DEFORMATIONS

This application is a continuation of PCT/ES96/00079 filed Apr. 9, 1996.

FIELD OF THE INVENTION

The present invention relates to a linear expander device usable in the progressive correction of deformations of the skull and of the face.

PRIOR ART

In 1969, Paul Tessier established the principles for the primary treatment of craniofacial deformations. Those principles have hardly changed up to the present time (Marchac).

In general terms these operations consist in multiple osteotomies which frequently require bone dismantling in the affected areas with a view to their subsequent rearrangement within criteria as close as possible to normality. Depending on the clinical case, the technique used, age, etc., the fixing of the bone fragments is carried out by means of mutual engagement, steel wire or, more recently, miniplates. Bone grafts are very frequently used for completing the structure and helping to fix and support the fragments.

These surgical techniques have drastically changed the prognosis of patients affected by congenital craniofacial deformations. Nevertheless, the experience gained over this period of time has revealed a number of short- and long-term problems for which definitive solutions have not yet been found. Among them we may cite:

1. The immediate increase in size of the cranial cavity with the creation of an extradural dead space, particularly after fronto-orbital surgery, with consequent risk of loss of cerebrospinal fluid, haematoma, infection, etc. A recent statistical study by H. M. Spinelly et al. ("An analysis of extradural dead space after fronto-orbital surgery". Plast. Reconstr. Surg. 93:1372, 1994) reports that the intracranial dead space is obliterated later than was previously thought, including in early infancy.
2. Bone growth disorders. Lack or limitation of regeneration, and even reabsorption. These surgical techniques involve very extensive dissection of soft portions and more particularly of the periosteum. Rupture of the osteoperiosteal complex damages both tissues, which, despite originating from two distinct tissue lines, provide a perfect example of symbiotic coexistence. The periosteum assists bone development via the cambrium and subsequently provides nutritive support to the bone cortex via its vascular network. In many cases, pieces of bone separated completely from the other tissues (periosteum and dura mater) behave like authentic free autografts, which in their ischaemic phase give rise to irreparable damage to the growth nuclei and encourage reabsorption and/or lack of regeneration. The process of reabsorption is also one of the causes of long-term failures of reconstructive techniques which use bone grafts.
3. In certain craniofacial malformations such as Crouzon's syndrome, Apert's syndrome and plagiocephaly, ocular motility disorders are very frequent. In some cases these alterations seem to be primary and due to alteration of the outer muscles of the eye, but in other cases, perhaps the majority, they are due to morphological disorders of the orbit, as demonstrated by the improvement of some of the alterations after corrective osteotomies. We also know, however, that these operations may worsen the situation or even create it and/or render it irreversible. This has been attributed to the fact that surgical manipulation of the orbital walls may cause change in the vectors of the extraocular muscles, resulting in a change in the alignment of the eyes and causing or modifying a squint ("Ocular abnormalities associated with unilateral coronal synostosis". An. of Plast. Surg. August 1994). We also think that violent distortion of muscle fibres causes a loss of active muscular tension and an increase in passive muscular tension, and also ischaemia, both of which will lead to degeneration of muscle fibres.
4. Finally, we shall cite the restrictive effects on bone growth which have recently been attributed to "rigid fixing" and to the possible migration of fixing materials used.

In the light of all of the foregoing it seemed logical to seek a therapeutic procedure which would avoid excessive surgical manipulation of tissues and would allow progressive and controlled correction of deformities. This has perhaps been the thinking which has guided some authors to begin the use in flat bones of "distraction" appliances with similar characteristics to those used in traumatology and orthopaedics for enchondral bones. These bone lengtheners (Howmedica Corp., Rutherford, M.) have been used chiefly in the jaw and only very exceptionally in other areas of the craniofacial skeleton.

If we accept that the ideal treatment for congenital craniofacial deformities will be by means of progressive expansion, the next step would be to design specific appliances for the purpose. These appliances might be of two types, viz. external and internal.

a) External Appliances

Appliances of this type are now in use both in the experimental field and in some clinical cases. The mechanism of action is based on the use of an endless screw similar to those used in traumatology and orthopaedics. These external appliances have the following disadvantages:

Risk of infection.

Fixing problems.

Inconvenience to the patient because they require continual cleaning maintenance and exquisite asepsis. They have to be prevented from becoming caught in clothing or other objects. They are unaesthetic.

These disadvantages increase in geometrical progression when two or more appliances are used simultaneously, as will be necessary in the majority of cases.

Examples of these devices are represented in the prior art (U1028050) and specifically in vertebral osteosynthesis (FR2697744), in soft bones (DE3936703), etc.

Internal Appliances

We have not found in the literature reviewed any reference relating to internal appliances.

The operating principle of the appliances which we have called "linear expanders" is similar to that of the soft-portion expanders which are currently on the market, viz. the introduction of an extensible globe into the interior of the tissues and its spatial increase by progressive injection of saline solution via a subcutaneous valve. Particularly well-known are the expanders used in increasing the volume of women's breasts. Descriptive references of these devices are to be found in patents EP183496, EP338701, EP324234, EP411767, all of them in the name of Dow Corning. The essential difference between the invention and the prior art lies in the fact that in conventional expanders the expansive force manifests itself multidirectionally, being limited only by hard anatomical structures and, in certain types of expanders, by non-elastic membranes situated in one of their faces. In contrast, in the "linear expanders" which are the subject of the present invention, energy is transmitted in a unidirectional direction. This circumstance of control of the direction of tissue expansion opens up unprecedented prospects for using these appliances for acting both on soft tissues and on the bony skeleton.

SUMMARY OF THE INVENTION

The expanders described in the present invention transmit energy in a linear direction. The appliances would be completely internal and would allow adjustment of the expansion process. They have to be as small and planar as possible and have smooth edges in order to prevent decubitus.

They could be made from various materials which are well tolerated by the human body. The first trials were carried out using silicone-type polymers, but biodegradable materials may also be included, which would obviate a second operation for extracting them. In any case, the time for extracting them might be estimated at between 6 months and 1 year and only a minor operation would be involved.

The advantages of progressive correction using an expansion device instead of the present practice of performing craniotomies may be summarized as follows.
1. Much quicker operation.
2. Far less traumatic and "almost" extracranial operation, since it is limited to one or more osteotomies with very little dissection of the periosteum, without detachment of the dura mater and without intra-operative bone mobilization.
3. Progressive enlarging of the cranial cavity without the risks involved in the creation of a dead space (haematomas, loss of cerebrospinal fluid, infection, etc.).
4. Precise control of deformity correction.
5. Progressive ossification at the level of the osteotomy lines during the expansion process, particularly in children.
6. Very little chance of interfering with subsequent bone growth, through avoiding bone manipulation and the risk of ischaemia and subsequent damage to ossification centres. Also through the elimination of rigid fixing elements and bone grafts.
7. Prevention of dysfunctions of the extensor muscles of the eye due to sudden elongations and to changes in force vectors.

DETAILED DESCRIPTION OF THE INVENTION

Figure 3:
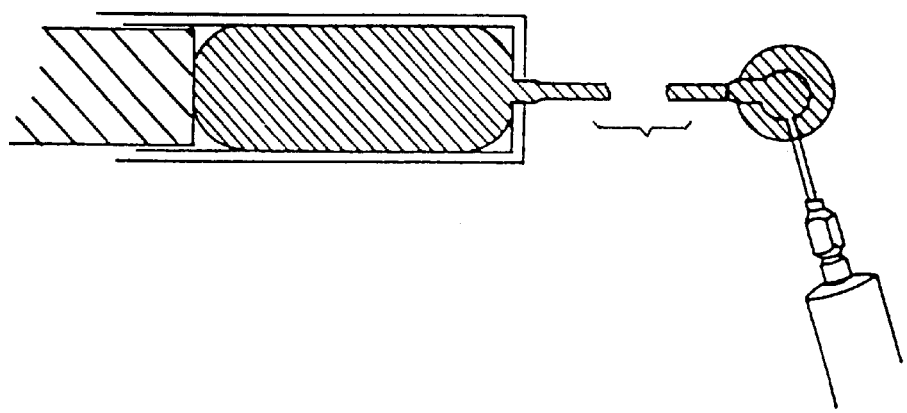

We shall describe below preferred embodiments of the present invention with reference to the following diagrams:

FIGS. 1–1A: View from above of the linear expander with four anchoring points (5), with movable element (4), fixed housing (9), element (1) which can be inflated by means of tube (2) connected at the fluid-injection point (3). Detail of the retaining-ratchet arrangement (8) between opposite walls.

FIG. 2: Detail of the hook-shaped movable and fixed separating ends (7 and 6) of the linear expander. Upper overlap (7') of the free end of the movable element.

FIG. 3: Representation of the movement of the movable element as a result of the hydraulic/pneumatic pressure exerted by the supply of fluid to the inflatable element.

Figure 4:
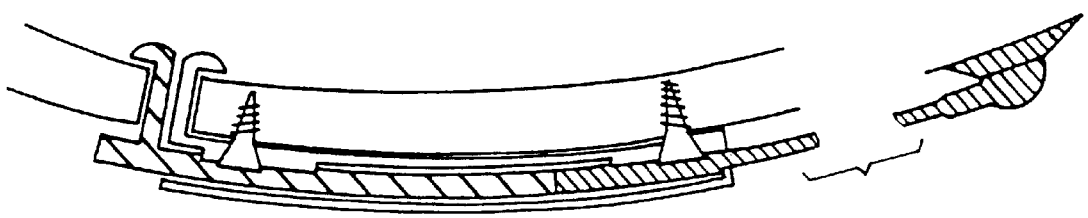

FIG. 4: Side view of the piston-type linear expander with hook-shaped end anchored to the skull bone.

Figure 5:
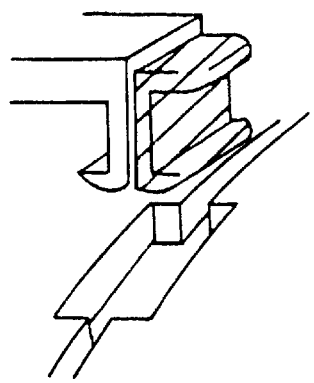

FIG. 5: Detail of the hook-shaped ends (fixed and movable) of the linear expander, and of the aperture for introducing them into the skull.

Figure 6:
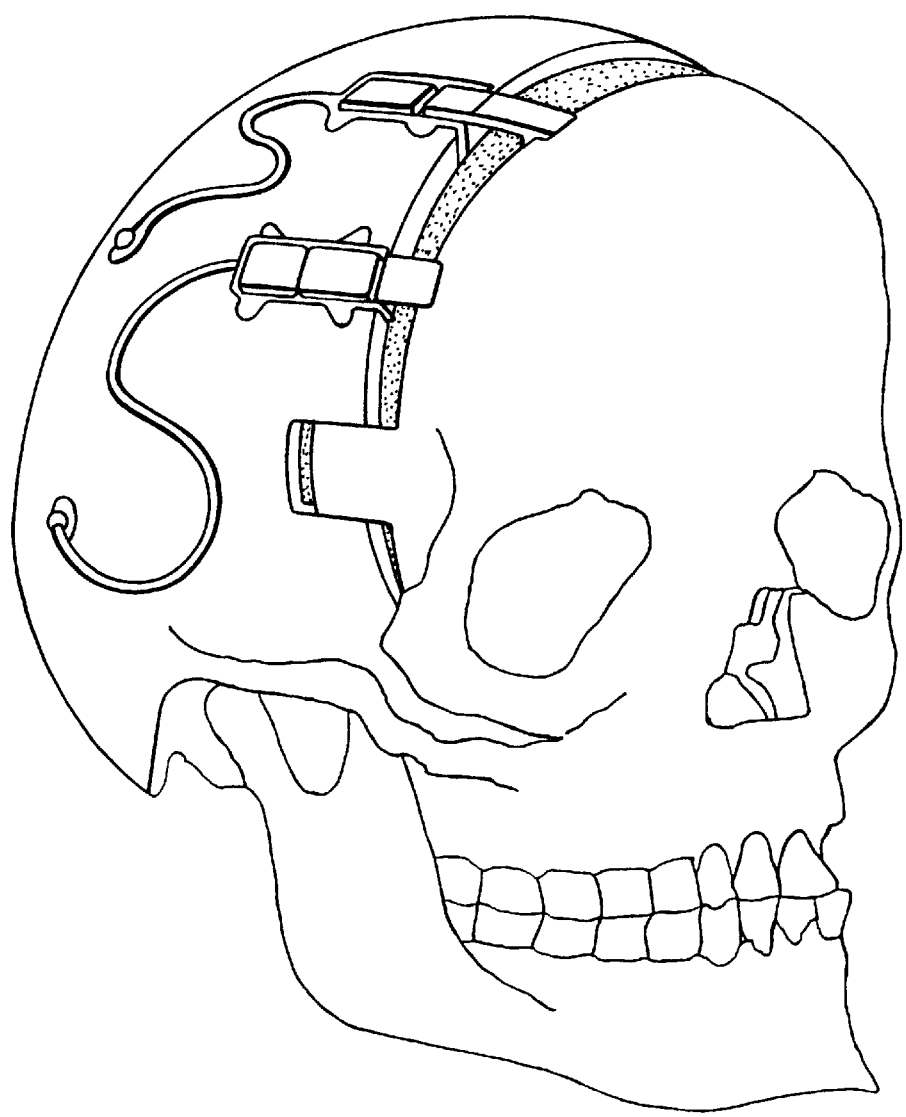

FIG. 6: Representation of the separating action exerted on skull bones by the combination of two piston-type linear expanders with hook-shaped ends.

FIGS. 7–7A: View from above of retractable linear expander with movable inner housing (10) and fixed outer housing (11) with only one anchoring point (5), with detail of the retaining-ratchet arrangement (8) between opposite walls.

FIG. 8: Side view of the foregoing expander device, showing the hook-shaped ends (6 and 7) of the two housings.

FIGS. 9–9A: View from above of piston-type linear expander with blunt end (4') for nasal corrections, with detail of the retaining-ratchet arrangement between opposite walls.

FIGS. 10–10A: Side view of piston-type linear expander with blunt end piston for nasal corrections, with detail of area of flexible connection to the tube (12).

Figure 11:
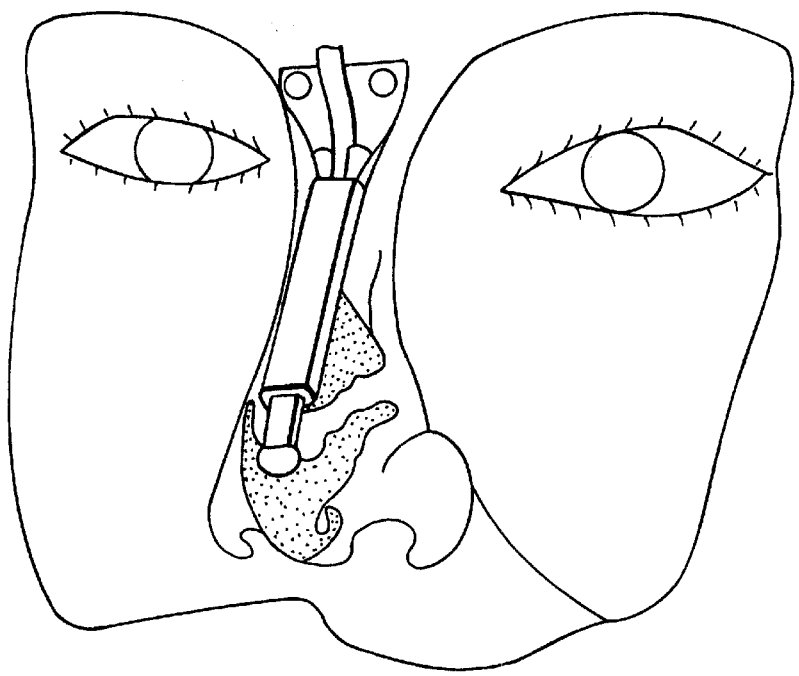

FIG. 11: Frontal representation of the piston-type linear expander with blunt end, when it has been inserted.

Figure 12:
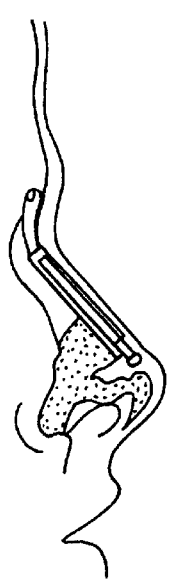

FIG. 12: Lateral representation of the piston-type linear expander with blunt end unextended, when it has been inserted.

Figure 13:
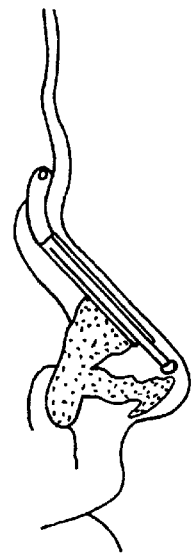

FIG. 13: Lateral representation of the piston-type linear expander with blunt end extended, when it has been inserted.

Referring first to FIGS. 1 to 6 of the invention, this type of appliance comprises a very elongate rectangular housing with very thin walls which are rigid or semi-rigid but are not extensible. The housing is closed at one end and open at the other. The closed portion accommodates a small globe (1) which communicates via a tube (2) with a valve (3) via which it is possible to inject a fluid. The remainder of the housing, constituting nearly ¾ of the latter, is occupied by a solid part (4) which is visible via the open extremity and which can slide along the inside of the housing.

The operating mechanism consists in dilation of the globe when a fluid is injected via the valve, with the result that the globe, being confined in a rigid cavity which is fixed on every side except one, expands via this latter side and acts as a piston, which in its turn drives the sliding part outwards.

For use in craniofacial surgery, the housing is provided with a number of lugs (5) which make it possible to fix it to bones by means of microscrews, and it has a hook (6) directed inwards at its open end and which bears on one end of the osteotomy. The sliding part is also provided with another hook-shaped edge (7) oriented in the opposite direction, which bears on the other end of the osteotomy. The free end also terminates in an overlap (7') which bears on the bony tissue being separated. The force exerted by the projection of the globe (1) when fluid is injected via the valve (3) will cause progressive separation of the osteotomy line and consequent expansion of the cranial cavity. Between the sliding part and its housing is arranged a ratchet-action mechanism (8) which prevents withdrawal of the sliding part (4) in the event of decrease or cessation of the pressure in the globe (1).

According to another variant of this invention, represented in FIGS. 7 and 8, the appliance comprises two very planar housings which are elongate in shape, with thin walls constructed, like the foregoing ones, of a material which is rigid or semi-rigid but not extensible. The two housings are each open at one of their extremities and are capable of being introduced into one another. The inner housing (10) accommodates throughout its extent a globe (1) which communicates via a tube (2) with a valve (3) via which it is possible to inject a fluid.

The operating principle is the same as that described in the embodiment of FIGS. 1 to 6 and consists in dilation of the globe when a fluid is injected via the valve. Said globe, being confined in the inner housing (10), expands via its open extremity and pushes the far wall of the outer housing (11) in the opposite direction, acting as a whole as a telescopic system provided also with a retaining-ratchet mechanism (8) between the two housings to prevent its withdrawal in the event of loss of pressure in the globe. Both the inner housing (10) and the outer housing (11) end in hook-shaped edges (6 and 7) which are oriented in opposite directions and which bear respectively on each of the ends of the osteotomy. The force transmitted by the injection of the fluid causes progressive dilation of the osteotomy line and consequent expansion of the cranial cavity or of the facial massif. The outer housing (11) is provided with a lug (5) which makes it possible for it to be fixed to the bone by means of a microscrew or a wire. Similar fixing may be necessary in some cases for the inner housing (10).

We have observed that the applications of the linear expanders which are the subject of the invention are not limited solely to the expansion of skull bones. They may also be used with some variants for the expansion of soft tissues, as in the case of very short nostrils of congenital, post-traumatic or iatrogenic origin. The embodiment of the expander represented in FIGS. 9 to 13 applies to this particular case. Within the same working principle as the preceding embodiments, the most significant modification consists in the elimination of the hook-shaped ends (6 and 7) and in the formation of a blunt thickening (4') at the end of the sliding part (4) in order to push the nasal cartilage.

Finally, the possibility is not excluded of using the invention in the lengthening and the correction of pathological incurvations of enchondral bones (long bones) and in the "directed" expansion of soft parts in other areas of the face, neck, scalp, trunk or extremities.

I claim:

1. In a linear expander for progressive correction of craniofacial deformations having a first element for anchoring to first bony tissue, a second element for anchoring to second bony tissue to be displaced relative to the first bony tissue, and means for relatively movingly the first and second elements longitudinally the improvement wherein the means comprises an inflatable element of flexible and elastic material for moving the first and second elements upon injection of a fluid.

2. The linear expander according to claim 1, wherein at lest one of the first and second elements has a free end shaped as a hook for the anchoring to the bony tissue.

3. The linear expander according to claim 1, wherein the first element comprises a flattened housing, the second element is for sliding tightly within the former and the inflatable element acts on a rear end of the second element.

4. The linear expander according to claim 1, wherein the second element has a solid structure and a prolongation to a free end for overlapping on top of the bony tissue to which it is anchored.

5. The linear expander according to claim 1, wherein the second element has a hollow structure with an open rear end and the inflatable element acts on a closed end of the first element.

6. The linear expander according to claim 1, wherein the means further comprises a ratchet mechanism between the first and second elements which prevents their movement in an opposite direction when pressure of the fluid injected in the inflatable element decreases or ceases after the relative movement longitudinally in one direction.

7. A linear expander for progressive correction of craniofacial deformations, the linear expander comprising:

means comprising first and second elements for relative longitudinal movement in one direction with respect to one another and respective tissue engagement, each of the elements having a first end portion and an opposite free end portion; and movement means including an inflatable actuator between end portions of the elements for causing the longitudinal movement, whereby to displace the tissue, upon injection of a fluid, wherein the inflatable element is a flexible and elastic material.

8. The linear expander according to claim 7, wherein the free end portion of at least the first element is hook shaped for the tissue engagement under an edge of a portion of bony tissue opposite a portion of the bony tissue of the tissue engagement of the second element.

9. The linear expander according to claim 7, wherein the first element is a housing of rectangular lateral cross section for the second element to fit tightly but longitudinally slidingly within the first element and the inflatable actuator is between the first end portions.

10. The linear expander according to claim 7, wherein the second element has solid surfaces, the second means for tissue engagement at its free end portion and a prolongation form its free end portion in a direction away from its first end portion for resting on top of bony tissue to be separated.

11. The linear expander according to claim 7, wherein the second element is a hollow structure with the first end portion open and the free end portion closed, the first end portion of the first element is closed, and the inflatable actuator is inside the hollow structure between the closed free end and the closed first end.

12. The linear expander according to claim 7, and further comprising means between the elements for preventing relative longitudinal movement of the elements in an opposite direction even when fluid pressure of the fluid injected into the inflatable actuator decreases or ceases.

13. The linear expander according to claim 8, wherein the first element is a housing of rectangular lateral cross section for the second element to fit tightly but longitudinally slidingly within the first element and the inflatable actuator is between the first end portions.

14. The linear expander according to claim 8, wherein the second element has solid surfaces, the second means for tissue engagement at its free end portion and a prolongation from its free end portion in a direction away from its first end portion for resting on top of bony tissue to be separated.

15. The linear expander according to claim 9, wherein the second element has solid surfaces, the second means for tissue engagement at its free end portion and a prolongation form its free end portion in a direction away from its first end portion for resting on top of bony tissue to be separated.

16. The linear expander according to claim 13, wherein the second element has solid surfaces, the second means for tissue engagement at its free end portion and a prolongation form its free end portion in a direction away from its first end portion for resting on top of bony tissue to be separated.

17. The linear expander according to claim 8, wherein the second element is a hollow structure with the first end portion open and the free end portion closed, the first end portion of the first element is closed, and the inflatable actuator is inside the hollow structure between the closed free end and the closed first end.

18. The linear expander according to claim 8, and further comprising means between the elements for preventing relative longitudinal movement of the elements in an opposite direction even when fluid pressure of the fluid injected into the inflatable actuator decreases or ceases.

19. The linear expander according to claim 9, and further comprising means between the elements for preventing relative longitudinal movement of the elements in an opposite direction even when fluid pressure of the fluid injected into the inflatable actuator decreases or ceases.

20. The linear expander according to claim 10, and further comprising means between the elements for preventing relative longitudinal movement of the elements in an opposite direction even when fluid pressure of the fluid injected into the inflatable actuator decreases or ceases.

21. The linear expander according to claim 11, and further comprising means between the elements for preventing relative longitudinal movement of the elements in an opposite direction even when fluid pressure of the fluid injected into the inflatable actuator decreases or ceases.

22. The linear expander according to claim 13, and further comprising means between the elements for preventing relative longitudinal movement of the elements in an opposite direction even when fluid pressure of the fluid injected into the inflatable actuator decreases or ceases.

23. The linear expander according to claim 14, and further comprising means between the elements for preventing relative longitudinal movement of the elements in an opposite direction even when fluid pressure of the fluid injected into the inflatable actuator decreases or ceases.

24. The linear expander according to claim 15, and further comprising means between the elements for preventing relative longitudinal movement of the elements in an opposite direction even when fluid pressure of the fluid injected into the inflatable actuator decreases or ceases.

25. The linear expander according to claim 16, and further comprising means between the elements for preventing relative longitudinal movement of the elements in an opposite direction even when fluid pressure of the fluid injected into the inflatable actuator decreases or ceases.

26. The linear expander according to claim 17, and further comprising means between the elements for preventing relative longitudinal movement of the elements in an opposite direction even when fluid pressure of the fluid injected into the inflatable actuator decreases or ceases.

* * * * *

UNITED STATES PATENT AND TRADEMARK OFFICE
CERTIFICATE OF CORRECTION

PATENT NO.  : 6,036,690
DATED       : March 14, 2000
INVENTOR(S) : Rafael DE LA PLAZA FERNANDEZ It is certified that error appears in the above-identified patent and that said Letters Patent is hereby corrected as shown below:

Title page, item [30], insert --

Foreign Application Priority Data April 11, 1995 [ES] Spain P9500724 --.

Signed and Sealed this

Sixth Day of February, 2001

*Attest:*

Q. TODD DICKINSON

*Attesting Officer*  *Director of Patents and Trademarks*